US 9,872,788 B2

(12) United States Patent
Carmeli et al.

(10) Patent No.: US 9,872,788 B2
(45) Date of Patent: Jan. 23, 2018

(54) DEVICE FOR PROTECTING HEMORRHOIDS

(75) Inventors: Ran Carmeli, Moshav Rinatya (IL); Moshe Klaiman, Gedera (IL)

(73) Assignee: Relief Therapies, Inc., Dover, DE (US)

( * ) Notice: Subject to any disclaimer, the term of this patent is extended or adjusted under 35 U.S.C. 154(b) by 0 days.

(21) Appl. No.: 14/115,642

(22) PCT Filed: Apr. 30, 2012

(86) PCT No.: PCT/IL2012/050152
§ 371 (c)(1),
(2), (4) Date: Nov. 5, 2013

(87) PCT Pub. No.: WO2012/150597
PCT Pub. Date: Nov. 8, 2012

(65) Prior Publication Data
US 2014/0081311 A1    Mar. 20, 2014

Related U.S. Application Data

(60) Provisional application No. 61/482,659, filed on May 5, 2011.

(51) Int. Cl.
*A61F 5/00*    (2006.01)
(52) U.S. Cl.
CPC .................. *A61F 5/0093* (2013.01)
(58) Field of Classification Search
CPC .................. A61B 1/31; A61B 17/0057; A61B 2017/22037; A61F 5/0093; A61F 6/146; A61F 5/08; A61M 25/04; A61M 27/00

USPC ....... 606/191, 197, 198, 200; 623/1.11, 1.12
See application file for complete search history.

(56) References Cited

U.S. PATENT DOCUMENTS

| 844,450 A | 2/1907 | Harris |
| 1,527,068 A | 2/1925 | Parsons |
| 2,499,045 A | 2/1950 | Walker et al. |
| 3,826,242 A | 7/1974 | Eggers |
| 3,831,583 A * | 8/1974 | Edmunds, Jr. ....... A61B 17/122 128/899 |
| 4,331,151 A | 5/1982 | Golden |

(Continued)

FOREIGN PATENT DOCUMENTS

| GB | 2295551 | * | 5/1996 |
| WO | WO 2005/044146 | | 5/2005 |

(Continued)

OTHER PUBLICATIONS

International Search Report and the Written Opinion Dated Aug. 31, 2012 From the Interntional Searching Authority Re. Application No. PCT/IL2012/050152.

(Continued)

*Primary Examiner* — Anh Dang

(57) ABSTRACT

According to one aspect of the present invention there is provided a device, preferably a disposable device, for reducing pain, bleeding and/or distension of hemorrhoids during defecation comprising an anchor portion being anchorable against tissue of a rectum and being attached to a tubular portion sized and configured for outwardly biasing internal hemorrhoids (i.e. pushing them against rectal/anal wall tissue) and optionally external hemorrhoids when the anchor portion is preferably anchored against the rectum wall.

15 Claims, 12 Drawing Sheets

(56) References Cited

U.S. PATENT DOCUMENTS

| | | |
|---|---|---|
| 4,341,211 A | 7/1982 | Kline |
| 4,686,985 A | 8/1987 | Lottick |
| 4,844,073 A | 7/1989 | Pohler |
| 4,932,958 A | 6/1990 | Reddy et al. |
| 5,263,926 A | 11/1993 | Wilk |
| 5,697,948 A | 12/1997 | Marin et al. |
| 5,817,124 A | 10/1998 | Karell |
| 5,924,423 A | 7/1999 | Majlessi |
| 5,941,860 A | 8/1999 | Wheeler |
| 6,364,852 B1* | 4/2002 | Lee ................................ 604/15 |
| 6,517,562 B1 | 2/2003 | Holland |
| 2001/0007082 A1* | 7/2001 | Dusbabek et al. ........... 623/1.11 |
| 2001/0014821 A1 | 8/2001 | Juman et al. |
| 2001/0027307 A1 | 10/2001 | Dubrul et al. |
| 2002/0192273 A1 | 12/2002 | Buseman et al. |
| 2004/0097866 A1 | 5/2004 | Kusano |
| 2005/0177214 A1 | 8/2005 | Pohler |
| 2006/0015171 A1* | 1/2006 | Armstrong .................... 623/1.12 |
| 2006/0036311 A1 | 2/2006 | Nakayama et al. |
| 2006/0167473 A1 | 7/2006 | Scheyer |
| 2007/0021820 A1* | 1/2007 | Sisken .......................... 623/1.11 |
| 2007/0106366 A1* | 5/2007 | Delaloye et al. ............. 623/1.11 |
| 2009/0022353 A1* | 1/2009 | Goldstein et al. ............. 381/380 |
| 2009/0043330 A1* | 2/2009 | To ................................. 606/194 |
| 2009/0171238 A1* | 7/2009 | Hanley et al. ................ 600/549 |
| 2009/0216337 A1* | 8/2009 | Egan .......................... A61F 2/04 623/23.64 |
| 2010/0249701 A1 | 9/2010 | Göbel |
| 2011/0160657 A1* | 6/2011 | Gobel .................... A61F 2/0013 604/96.01 |

FOREIGN PATENT DOCUMENTS

| | | |
|---|---|---|
| WO | WO 2009/144028 | 12/2009 |
| WO | WO 2010/020985 | 2/2010 |
| WO | WO 2012/150597 | 11/2012 |

OTHER PUBLICATIONS

International Preliminary Report on Patentability Dated Nov. 14, 2013 From the Interntional Bureau of WIPO Re. Application No. PCT/IL2012/050152.

Office Action and Search Report Dated Feb. 25, 2014 From the Israel Patent Office Re. Application No. 229272 and Its Translation Into English.

Office Action Dated Jul. 20, 2014 From the Israel Patent Office Re. Application No. 229272 and Its Translation Into English.

Supplementary European Search Report Dated Nov. 17, 2014 From the European Patent Office Re. Application No. 12779337.0.

* cited by examiner

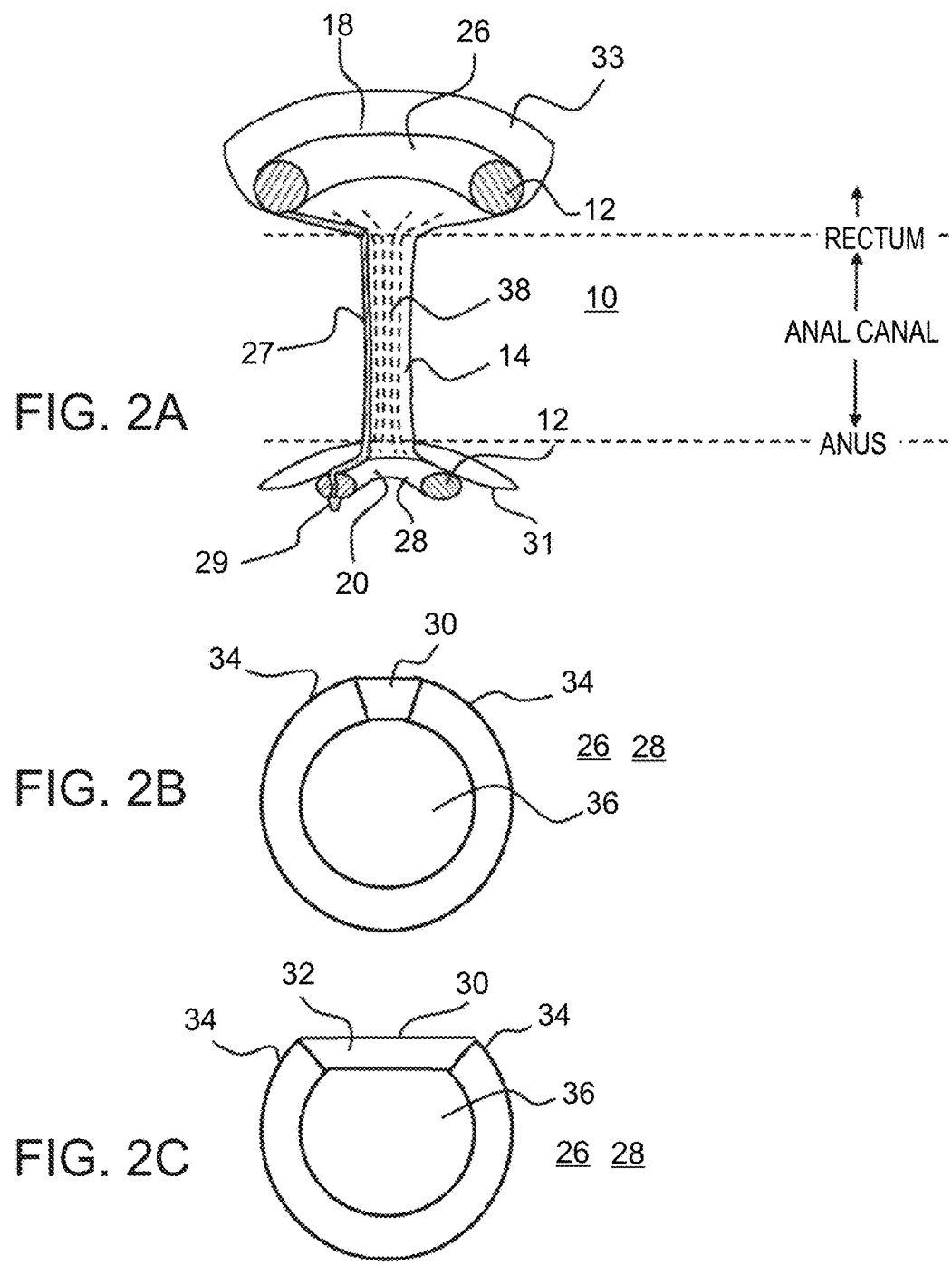

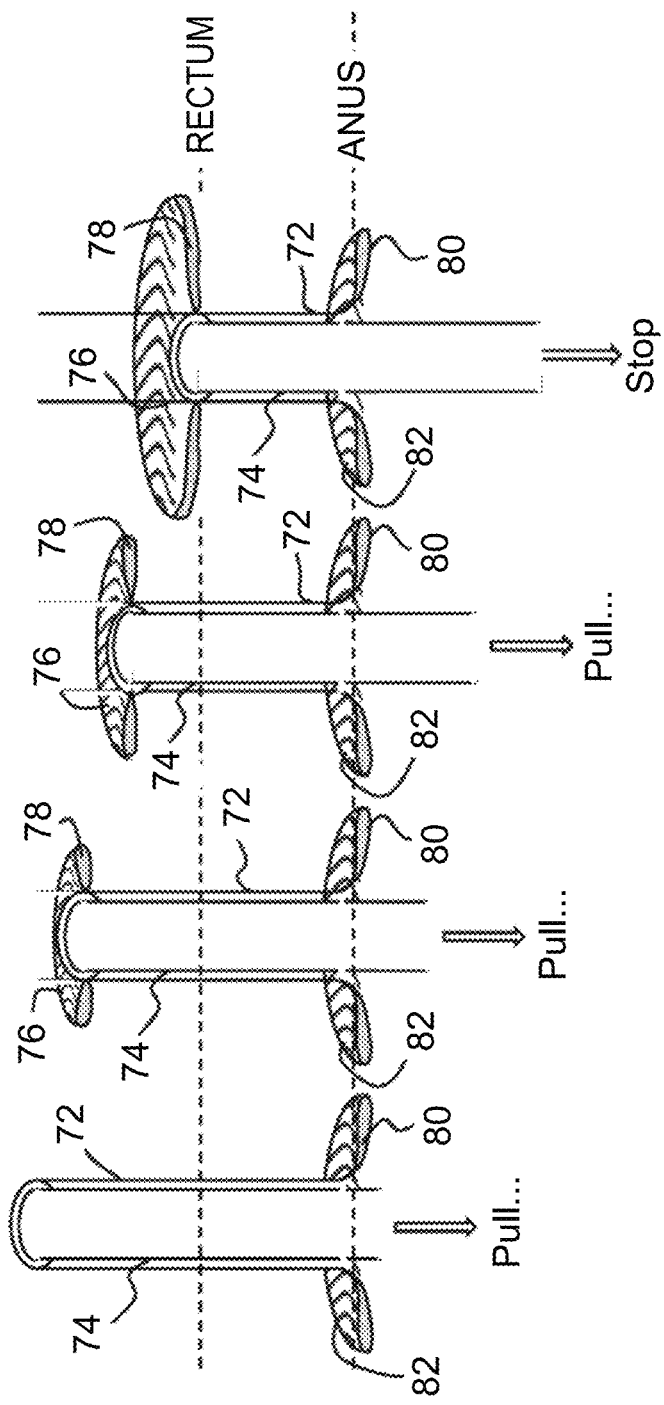

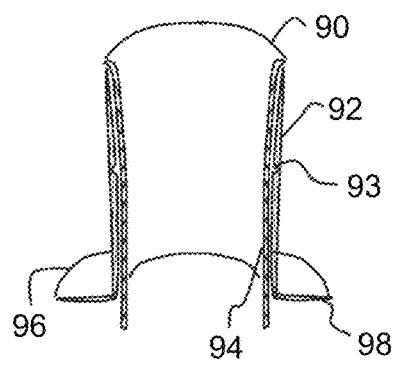
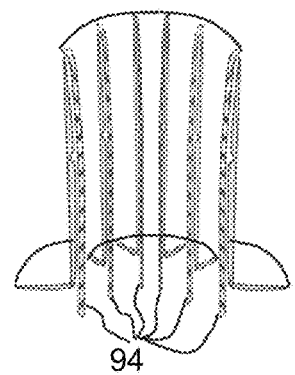
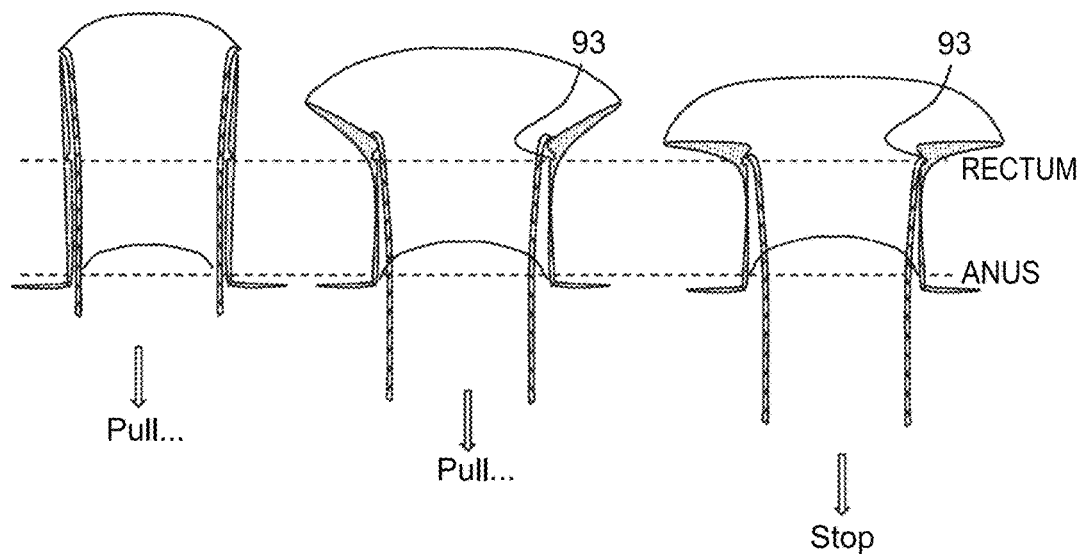

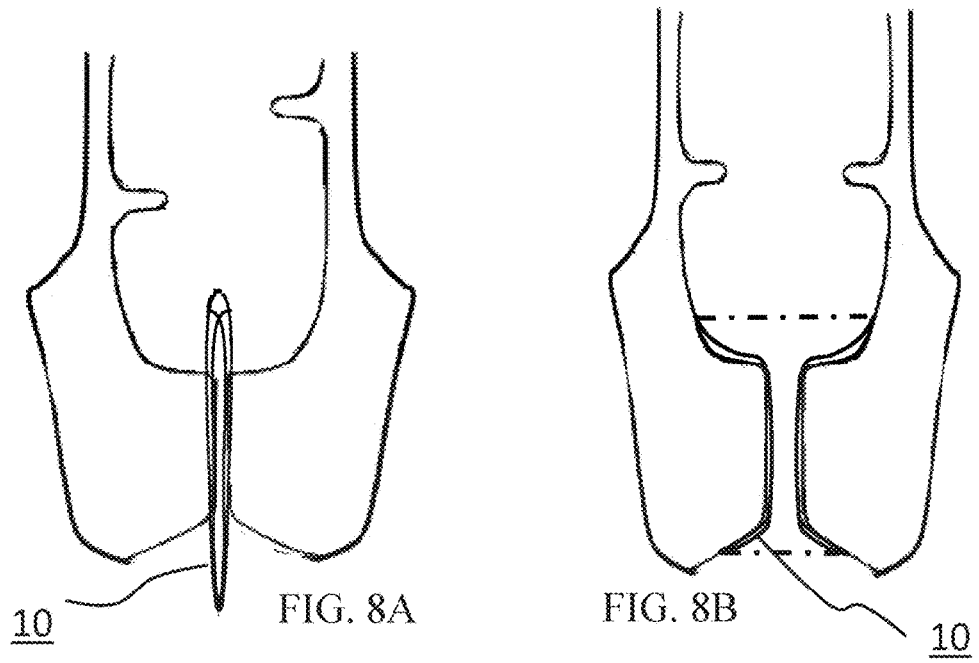

DEVICE FOR PROTECTING HEMORRHOIDS

RELATED APPLICATIONS

This application is a National Phase of PCT Patent Application No. PCT/IL2012/050152 having International filing date of Apr. 30, 2012, which claims the benefit of priority under 35 USC §119(e) of U.S. Provisional Patent Application No. 61/482,659 filed on May 5, 2011. The contents of the above applications are all incorporated by reference as if fully set forth herein in their entirety.

FIELD AND BACKGROUND OF THE INVENTION

The present invention relates to a device for protecting hemorrhoids during defecation and more specifically to an anal canal-positioned device that biases internal hemorrhoids against the canal wall and thus prevents swelling and/or prolapse and/or irritation of internal and optionally external hemorrhoids caused by physical straining and/or defecation.

Hemorrhoids are anal canal wall structures which are composed of arterio-venous channels and connective tissue and serve as cushions to aid the passage of stool.

Hemorrhoids become pathological when swollen or inflamed; pathological hemorrhoids are often referred to as piles. The symptoms of pathological hemorrhoids depend on hemorrhoid type. Internal hemorrhoids typically present as painless rectal bleeding while external hemorrhoids present with pain in the area of the anus.

External hemorrhoids occur at the distal end of the anal canal near the anal orifice. External hemorrhoids are varicosities of the veins draining the inferior rectal arteries, which are branches of the internal pudendal artery. They are sometimes painful, and often accompanied by swelling and irritation. Itching, although often thought to be a symptom of external hemorrhoids, is more commonly due to skin irritation. External hemorrhoids are prone to thrombosis: if the vein ruptures and/or a blood clot develops, the hemorrhoid becomes a thrombosed hemorrhoid.

Internal hemorrhoids occur in the dentate line, which is the anatomical landmark at the boundary between the anal canal to the rectum, and are varicosities of veins draining the superior rectal arteries. Since this region lacks pain receptors, internal hemorrhoids are usually not painful, however, they may bleed when irritated and or swollen. Untreated internal hemorrhoids can lead to two severe forms of hemorrhoids: prolapsed and strangulated hemorrhoids. Prolapsed hemorrhoids are internal hemorrhoids that are distended and pushed outside the anus. If the anal sphincter muscle goes into spasm and traps a prolapsed hemorrhoid outside the anal opening, the supply of blood is cut off, and the hemorrhoid becomes a strangulated hemorrhoid.

One main cause of prolapsed hemorrhoids is straining, caused by, for example, defecation. For people who suffer from hemorrhoids, defecation, resulting in hemorrhoids prolapse, is not only painful, but a daily trigger to the progression of the disease. Defecation may also lead to bleeding of hemorrhoids, due to contact between fecal matter and hemorrhoidal tissue.

Internal hemorrhoids are typically classified as follows: grade I—no prolapse, grade II—prolapse upon defecation but spontaneously reduce, grade III—prolapse upon defecation and need for manual reduction, and grade IV—prolapsed and cannot be manually reduced.

Hemorrhoid treatment typically involves an increase in fiber intake, oral fluids to maintain hydration, NSAID analgesics, sitz baths, and rest. Surgery is reserved for cases that fail to improve following such treatment.

Although present treatment approaches are somewhat effective in reversing pathological hemorrhoids, there remains a need for treatment that prevents formation or progression of hemorrhoids and in particular internal hemorrhoids.

SUMMARY OF THE INVENTION

According to one aspect of the present invention there is provided a device, preferably a disposable device, for reducing pain, bleeding and/or distension of hemorrhoids during defecation comprising an anchor portion being anchorable against tissue of a rectum and being attached to a tubular portion sized and configured for outwardly biasing internal hemorrhoids (i.e. pushing them against rectal/anal wall tissue) and optionally external hemorrhoids when the anchor portion is preferably anchored against the rectum wall.

According to another aspect of the present invention there is provided a device, preferably a disposable device, for treatment of constipation/easing the defecation comprising an anchor portion being anchorable against tissue of a rectum and being attached to a tubular portion sized and configured for outwardly biasing the anal canal (i.e. pushing outwards the walls of the anal canal) and supporting its broadening to ease the strain and pain of constipation) when the anchor portion is anchored against the rectum wall.

According yet another aspect of the present invention there is provided a device, preferably a disposable device, for preparing the anal canal for medical rectal treatment and/or procedures, easing the pain and discomfort caused during such treatments, being anchorable against tissue of a rectum and being attached to a tubular portion sized and configured for outwardly biasing the anal canal (i.e. pushing outwards the walls of the anal canal) and shielding the anal canal and lower rectum from being touched and stipulated by the medical treatment tools, when the anchor portion is anchored against the rectum wall.

According to further features in preferred embodiments of the invention described below, the anchor portion applies a radial force to the tissue of the rectum.

According to still further features in the described preferred embodiments the anchor portion includes one or more inflatable chambers.

According to still further features in the described preferred embodiments the one or more inflatable chambers form a continuous or discontinuous toroid.

According to still further features in the described preferred embodiments the inflatable chamber or chambers form a continuous or discontinuous conical toroid.

According to still further features in the described preferred embodiments the discontinuous toroid is substantially C-shaped.

According to still further features in the described preferred embodiments the discontinuous toroid is segmented.

According to still further features in the described preferred embodiments the anchor portion is a radially expandable wire mesh.

According to still further features in the described preferred embodiments the anchor portion is a radially expandable wire mesh housing a radial type spring/flexible member.

According to still further features in the described preferred embodiments the device further comprises a fluid conduit capable of communicating fluid from a proximal portion of the tubular portion to the one or more inflatable chambers.

According to still further features in the described preferred embodiments the device further comprises a substance capable of expanding the expandable device and thus applying pressure. The substance can be, for example, one that has expandable properties when contacted with fluid.

According to still further features in the described preferred embodiments the anchor portion does not extend below a dentate line when anchored to the tissue of the rectum.

According to still further features in the described preferred embodiments the tubular portion is a non-inflatable sleeve.

According to still further features in the described preferred embodiments the device further comprises a mechanism for biasing the tubular portion against the internal hemorrhoids and optionally the external hemorrhoids.

According to still further features in the described preferred embodiments the tubular portion is made from a braided material.

According to still further features in the described preferred embodiments the braided material is made of plastic and/or a metal.

According to still further features in the described preferred embodiments the inflatable portions are made from compliant, semi-compliant or non-compliant materials.

According to still further features in the described preferred embodiments the entire device is inflatable.

According to still further features in the described preferred embodiments the mechanism includes longitudinal struts attached to or embedded in at least a portion of the tubular portion.

According to still further features in the described preferred embodiments the entire device or a portion thereof is coated with a drug.

According yet another aspect of the present invention there is provided a device for reducing pain, bleeding and/or distension of hemorrhoids during defecation and optionally straining, comprising a balloon configured for anchoring within a lower rectum of a subject when inflated, the balloon being attached to a tubular mesh structure being substantially non-elastic along a longitudinal axis and elastic along a radial axis thereof.

According to still further features in the described preferred embodiments the tubular mesh structure extends from the lower rectum and into an anal canal when the balloon is inflated and anchored in the lower rectum.

According to still further features in the described preferred embodiments the tubular mesh structure is coated with silicone.

According to still further features in the described preferred embodiments the tubular mesh structure is fabricated from polyester or nylon.

According to still further features in the described preferred embodiments the tubular mesh structure is fabricated from a metallic material selected from the group consisting of stainless steel, nitinol, and cobalt chromium.

According to still further features in the described preferred embodiments the balloon is a toroidal balloon.

According to still further features in the described preferred embodiments the toroidal balloon includes a conically shaped opening.

According to still further features in the described preferred embodiments the balloon is a non-compliant balloon.

According to still further features in the described preferred embodiments the device further comprises a tubular sheath for radially constraining the tubular mesh structure in a folded configuration.

According to still further features in the described preferred embodiments the tubular sheath includes a mechanism for releasing the tubular mesh structure from the folded configuration.

According to still further features in the described preferred embodiments the mechanism tears the sheath.

According to still further features in the described preferred embodiments the mechanism removes the sheath.

According to still further features in the described preferred embodiments the balloon is inflated to at least 2 ATM.

According to another aspect of the present invention there is provided a method of reducing pain, bleeding and/or distension of hemorrhoids comprising positioning the device described herein in the anal canal and rectum prior to straining or defecation.

According to yet another aspect of the present invention there is provided a method of treating constipation, comprising positioning the device described herein in the anal canal and rectum prior to straining or defecation.

According to yet another aspect of the present invention there is provided a method of preparing and shielding of the anal canal and lower rectum before medical treatments and/or procedures, comprising positioning the device described herein in the anal canal and rectum prior to straining or defecation.

According to yet another aspect of the present invention there is provided a system for reducing pain, bleeding and/or distension of hemorrhoids during defecation comprising the device described herein and an applicator for positioning and deploying the device in an anal canal-rectum region of a subject.

According to yet another aspect of the present invention there is provided a system for treating constipation, comprising the device described herein and an applicator for positioning and deploying the device in an anal canal-rectum region of a subject.

According to yet another aspect of the present invention there is provided a system for preparing and shielding of the anal canal, prior and during rectal medical treatments and/or procedures, comprising the device described herein and an applicator for positioning and deploying the device in an anal canal-rectum region of a subject.

According to still further features in the described preferred embodiments the applicator disengages from the device upon inflation of the balloon. Such disengagement can be effected via controlled ripping of the applicator.

The present invention successfully addresses the shortcomings of the presently known configurations by providing a device capable of shielding hemorrhoids from swelling by applying a counter pressure on the hemorrhoids, and by shielding the friction exerted by stool during defecation while being easily applicable without causing discomfort during application and use.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2A-C illustrate one embodiment of the present device (FIG. 2A) which includes inflatable anchors shaped as a discontinuous toroidal balloon and its adaptability to small and large rectum diameters (FIGS. 2B and 2C respectively); dashed lines illustrate positioning of the device with respect to anus, anal canal and rectum.

FIGS. 6A-D illustrate intra-body deployment of another embodiment of the present device which includes a mesh-like device body.

FIGS. 7A-E illustrate intra-body deployment of yet another embodiment of the present device which includes a mechanical folding/locking device body.

FIGS. 8A-B illustrate the intra-body position of the present device in a pre-deployed (FIG. 8A) and deployed (FIG. 8B) states.

DESCRIPTION OF THE PREFERRED EMBODIMENTS

Figure 1:
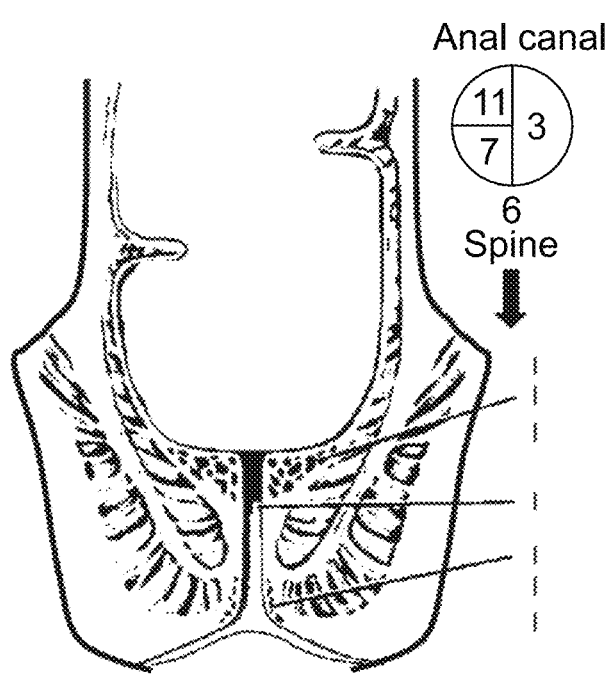
FIG. 1 is a prior art illustration of the anal canal and rectum regions of a human subject.

The present invention is of a device which can be used to prevent progression of internal hemorrhoids as well as reduce or prevent bleeding or pain associated therewith.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Numerous surgical and non-surgical approaches for treating internal and external hemorrhoids are known in the art.

Devices for preventing the progression of hemorrhoids which is caused by defecation are also known. U.S. Pat. No. 3,826,242 describes a tubular member that is inserted into the anal canal/rectum in order to serve as a hemorrhoidal barrier during defecation. The tubular member is maintained in the anal canal via a support that engages the toilet seat or via inflatable walls that exert pressure on anal canal tissue and a flared region that engages tissue around the rectal opening. U.S. Pat. No. 1,527,068 describes a simple tubular member that is positionable via an insert member in the anal canal/rectum and is used to protect the hemorrhoids during bowel movement.

Although the above described prior art devices can in theory shield hemorrhoids from fecal matter during defecation, their design suffers from several inherent limitations which limit their applicability and use.

While reducing the present invention to practice, the present inventors have carefully studied the anatomy and function of the anal canal and rectum and have devised a hemorrhoid-shield device which is capable of protecting hemorrhoids from distension, bleeding and pain during defecation and yet is easily deployable and does not cause discomfort during use.

To traverse the limitations of prior art devices, the present inventors have followed several important parameters in designing the present device:

(i) anchoring should be outside the anal canal since this region is sensitive to mechanical stimulation, e.g. above the dentate line and/or outside the anal orifice; also, the anatomy of the lower rectum will facilitate anchoring since it is slightly larger in diameter than the anal canal.

(ii) device should:
 a. actively bias hemorrhoids against canal wall;
 b. actively support the opening of the anal canal during constipation; and/or
 c. prepare and/or shield the anal canal prior to and during rectal medical treatments and/or procedures.

(iii) the portion of the device covering the hemorrhoids should be pliable and thin with a smooth internal surface to facilitate passage of stool, optionally it should be lubricated or firmly biasing the anal canal wall to support and ease the pain during constipation.

(iv) positioning of the device and deployment is done by the user himself, and the anchoring should be rapid and easy with minimal risk of inaccurate positioning;

(v) anchoring should be designed to maintain the device in place during defecation and/or treatment, without causing discomfort and damage to gastrointestinal (GI) tissue and without having to rely on external devices to maintain position;

(vi) device should be capable of accommodating for movements of rectal and anal tissue and for movement of fecal matter therethrough;

(vii) insertion of the device should be quick, easy and painless; and (viii) inflating/expanding of the device should be quick, easy and painless; and (ix) removal of the device should be quick, easy and painless.

Thus, according to one aspect of the present invention there is provided a device for preventing hemorrhoidal prolapse during straining as well as protecting hemorrhoids from prolapse during straining and for preventing/reducing the mechanical pressure on hemorrhoids caused by passage of stool.

The present device includes at least one anchor portion which is positionable above and/or below the anal canal (e.g. in the rectum above the dentate line and/or outside the anal orifice, see FIG. 2a) and a tubular portion (e.g. sleeve) that covers the internal and optionally external hemorrhoids and forcibly biases them against the canal wall (radially).

FIGS. 2-9b illustrate several embodiments of the present device which is referred to herein as device 10.

FIGS. 2a-e illustrate an embodiment of device 10 which includes one or more inflatable chambers forming anchor portion(s) 12 and a sleeve portion 14. Sleeve 14 is generally biased against the anal canal and/or hemorrhoids, and may optionally include support and/or biasing struts 38 or one or more inflatable chamber(s) to facilitate biasing. Furthermore, struts 38 provide sleeve 14 of device 10 with longitudinal support which assists in anchoring as is further described hereinbelow.

FIG. 2a is a cross section of Device 10 in a deployed state and positioned spanning a portion of the rectum and the anal canal. When in position, distal portion 18 of device 10 resides above the rectal neck, preferably above the dentate line (FIG. 1), while proximal portion 20 resides outside the anal canal and is in contact with tissue surrounding the anal orifice (e.g. skin surrounding anal orifice). Sleeve portion 14 spans the anal canal and is attached between anchor portions 12.

FIG. 2a illustrates a presently preferred configuration of device 10 which includes two anchor portions 12 interconnected by sleeve 14; anchor portions 12 are configured as a distal anchoring balloon 26 and a proximal anchoring balloon 28. Sleeve 14 can extend beyond anchor portions 12 to form proximal skirt 31 and distal skirt 33.

Distal anchoring balloon 26 and proximal anchoring balloon 28 can be filled through one or more lumen(s) 27 (one shown) capable of communicating fluid such as air, gas, water or saline to distal anchoring balloon 26 and proximal anchoring balloon 28 from one or more filling port (s) 29 (one shown) positioned at a proximal portion 20 of device 10.

In order to maintain device 10 within the anal canal/ rectum especially during defecation or constipation, distal anchoring balloon 26 is configured for applying a radial (outward) force against rectal wall tissue (mucosa) when expanded.

Since the rectum and anal canal expand (in diameter) to accommodate for fecal matter during defecation/constipation, distal anchoring balloon 26 is designed to accommodate for such expansion and maintain anchoring.

FIGS. 2b-c illustrate one configuration of distal anchoring balloon 26 which is capable of maintaining anchoring when the rectum and anal canal are collapsed (devoid of fecal matter) and when they are distended by fecal matter. Distal anchoring balloon 26 and/or proximal anchoring balloon 28 are shaped as a toroidal balloon (FIG. 2b) which is capable of elastically deforming and opening. Preferably, in order to provide a super elastic/super compliance structure, the toroidal balloon is formed from a discontinuous balloon (e.g. C-shaped) as shown in 2b and 2c. Gap 30 in distal anchoring balloon 26 can be unoccupied or it can include an elastic element 32 (as shown in FIGS. 2b-c) which is attached to ends 34 of the discontinuous toroidal balloon. Such an element 32 elastically stretches when fecal matter transits through opening 36 and thereby maintains sealing of distal anchoring balloon 26 against rectal mucosa. Element 32 can alternatively be an elastic biasing element (spring) that biases ends 34 outwardly and thus opens gap 30 and maintains distal anchoring balloon 26 biased against rectum when the rectum increases in diameter (to accommodate for fecal matter movement therethrough).

It will be appreciated that although distal anchoring balloon 26 of FIGS. 2a-c is formed from a single (gapped) expandable chamber, other configurations including two or more (gapped) chambers optionally interconnected via elastic or sprung elements are also envisaged herein. Thus, distal anchoring balloon 26 can be formed from a toroidal balloon including 1, 2, 3, 4, 5 or 6 separate chambers.

In the configuration shown in FIG. 2a, distal anchoring balloon 26 and proximal anchoring balloon 28 are surrounded by skirt 33 and skirt 31 (respectively). Skirts 31 and 33 extend beyond the regions of balloon anchoring to provide additional anchoring forces (frictional) and to improve the sealing against the rectal mucosa (at distal portion 18 of device 10) and against the skin outside the anal orifice (at proximal portion 20 of device 10). Skirts 31 and 33 are further described hereinbelow.

Anchoring can alternatively be achieved by placing a (continuous) toroidal balloon in a region of the rectum which is capable of accommodation, e.g. where the wall tissue is pliable and capable of accommodating a large diameter balloon. The diameter of such a balloon (when inflated) will be selected larger than the typical maximum diameter of the anal canal during defecation (e.g. about 40 mm). Additional anchoring and longitudinal integrity provided to device 10 by sleeve 14 fitted with struts 38 will prevent balloon 26 from "flipping" and being pushed out during defecation.

Anchoring is maintained by matching the pressure of balloon 26 with defecation pressure inside the rectum [typically 0.5-4 atmospheres (atm)].

Skirt 33 will be forced against the rectal wall by fecal matter during defecation/constipation providing an additional anchoring force. In addition, pressure applied to skirt 33 by balloon 26 will force skirt 33 to firmly adhere to the rectal wall tissue.

Anchoring can also be enhanced by varying the surface texture and frictional coefficient of the inner (facing feces) and outer (facing GI tissue) surfaces of device 10. Inner surfaces which come in contact with fecal matter are preferably coated/formed to provide low friction forces (e.g. by using a Teflon based materials), while the outer surfaces which come in contact with rectal and anal canal tissue are coated/formed to provide high frictional forces (e.g. by using silicon based materials). Thus, during defecation, frictional forces between device 10 and fecal matter moving therethrough will be very low thereby facilitating passage, while radial (expansion) pressure exerted by fecal matter on device 10 (and balloon 26 on skirt 33) and the high frictional forces between device 10 and the tissue will assist in anchoring device 10 in position.

Figure 2D:
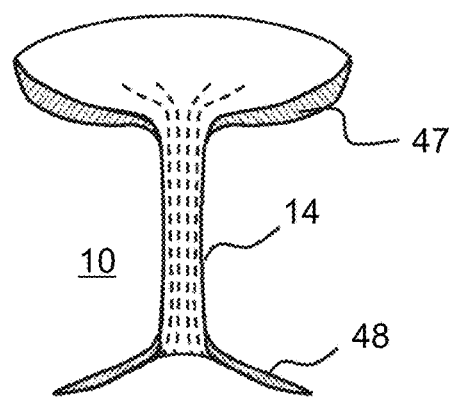
FIGS. 2D-E illustrate embodiments of the present device which include alternative balloon anchor and skirt configurations.
Figure 2E:
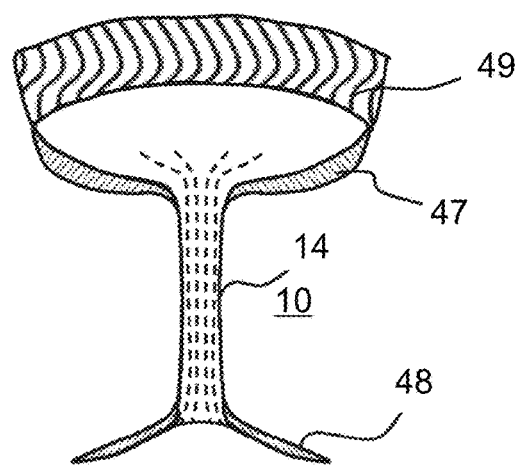

FIGS. 2d-e illustrate alternative cross sectional shapes for anchoring balloons 47 and 48. FIG. 2e illustrates an alternative skirt 49 configuration.

Balloons 26 and 28 can be fabricated from compliant materials (e.g. polyurethane and/or silicon); semi compliant materials (e.g. nylon resin and/or PEBAX) or non compliant materials (PET) or any combinations thereof. The balloons can be fabricated using blow-molding, extrusion or thermal bonding approaches. Balloons 26 and 28 can have an external diameter in the range of 30-60 mm, an internal diameter of 20-55 mm and a cross section diameter (e.g. height) of 2-10 mm. Inflation pressure of such balloons depends on the material and production approaches used. For example, a complainant balloon anchor (e.g. silicon/polyurethane) can be inflated to a pressure of 1-5 atmospheres, while semi-compliant or non-compliant balloon anchors can be inflated to 20 atmospheres. A typical inflation pressure for balloon 20 and 26 can be in the range of 1-5 atm.

Proximal anchoring balloon 28 can be configured similarly to distal balloon, but since it is positioned outside the anal canal it can be formed from a continuous toroidal balloon with an opening 36 having an external diameter of 30-60 mm and an internal diameter of 20-55 mm.

It will be appreciated that although a balloon-type proximal anchor portion is presently preferred, other forms of anchors using spring type materials, adhesives tapes and the like can also be used in the proximal anchoring portion of device 10.

Sleeve 14 can be fabricated from materials similar or identical to those described above. Preferred materials include semi-compliant silicon and polyurethane. Sleeve 14 can be produced via extrusion, molding and the like. Sleeve 14 can be bonded to balloons 26 and 28 (e.g. using thermal bonding/welding or adhesives). Sleeve 14 is typically 20-60 mm in length with a diameter of about 30 mm when pushed open (e.g. by feces) and 2-16 mm when collapsed.

As shown in FIGS. 2a-c, sleeve 14 can optionally include struts 38. Struts 38 run along the length of sleeve 14 (i.e. along a longitudinal axis thereof) and as such provide longitudinal integrity and column strength to the sleeve 14. Struts 38 provide sleeve 14 with flexibility in the radial direction and thus enables it to easily comply with the anatomy during defecation. The number of struts 38 varies with a range of 4-16. Struts 38 can be evenly or non-evenly distributed around a circumference of sleeve 14 and can be optionally radially connected with flexible connecting members that do not limit the radial compliancy of the sleeve. Struts 38 can be fabricated from a material that provides the longitudinal rigidity necessary to prevent inversion of sleeve 14 and balloon 26. Exemplary materials include stainless steel, Nitinol, polymers and the like. The struts can be fabricated having a round or square cross sectional shape with a diameter of typically 0.3 to 2 mm. Struts 38 can be embedded within the material of sleeve 14 (e.g. sleeve 14 can be overmolded onto struts 38), or attached on an external and/or internal surfaces of sleeve 14. Struts 38 are designed such that upon expansion of upper and lower anchoring regions of device 10 (e.g. balloons 26 and 20) ends of struts 38 remain secured to balloons 20 and 26 while the midportions of struts 38 flex about 1-10 mm toward the anal canal tissue. This ensures that struts 38 effectively bias sleeve 14 against anal canal walls in general and against the hemorrhoids in particular.

Sleeve can alternatively or additional include one or more inflatable chambers (not shown) which can provide sleeve 14 with the additional rigidity and shape necessary to apply the biasing force to the hemorrhoids.

Figure 3A:
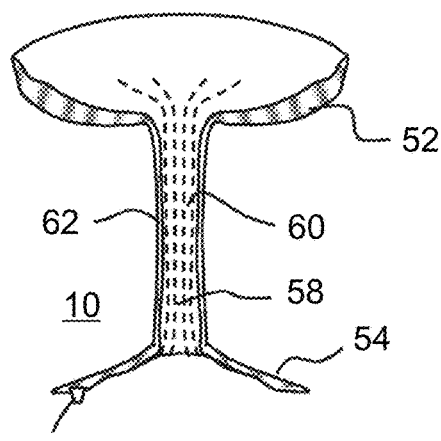
FIGS. 3A-C illustrate another embodiment of the present device which employs a sleeve having inflatable chambers.
Figure 3B:
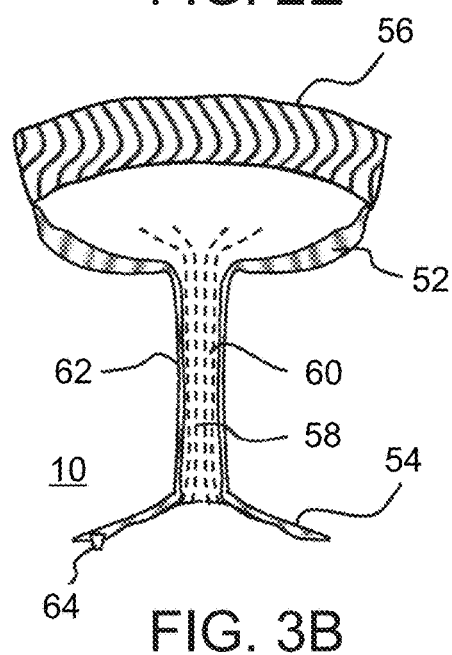

FIGS. 3a and 3b, illustrate a device 10 in which sleeve 14 includes inflatable member 62 which is connected between a distal anchoring balloon 52 and a proximal anchoring balloon 54. Such configuration can improve the biasing on the anal canal. Addition of struts 58 can also improve device 10 integrity (in the longitudinal axis) as well as increase biasing of sleeve 14 against anal canal tissue. FIG. 3b illustrates an upper skirt 56. The central inflatable section 62, may be inflated by a fluid such as water and/or air or it can self inflate upon wetting by the mucosa.

Figure 3C:
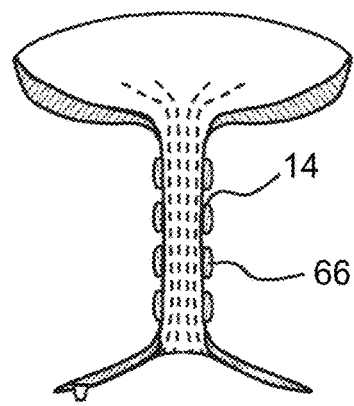

FIG. 3c illustrates a similar device 10, in which sleeve 14 includes several radially-disposed inflatable members 66 longitudinally spaced between the anchoring balloons. Such segmented inflatable members 66 can enhance the compliance to anal canal anatomy and biasing against hemorrhoids of device 10.

Figure 4:
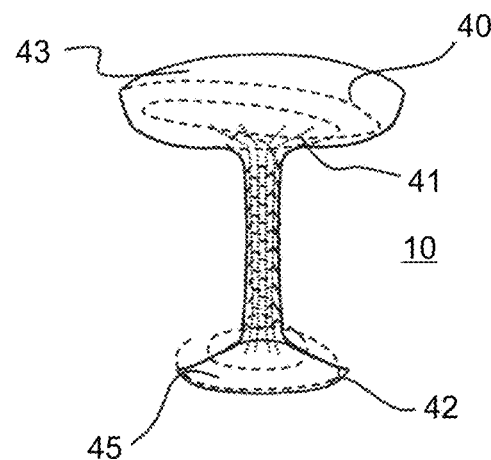
FIG. 4 illustrates an embodiment of the present device which includes spring coils anchors and sleeve.

FIG. 4 illustrates another embodiment of device 10 which includes an elastic wire/strut structure covered with a membrane.

Such devices can be manufactured by an elastic and/or super elastic alloys or polymers such as Nitinol, Stainless Steel, Nylon etc. . . . Sizes and shape are designed to provide the radial forces distribution along the device axis. Typically the upper portion of the device 40 will be expanded to a diameter of 30-60 mm, while the central portion of the device will be biased against the anal canal covering a typical range of 2-30 mm.

Mesh structure includes anchor portions 14 which in this case are formed as distal coil 40 and proximal coil 42. Coils 40 and 42 extend from ends of a wire tube structure 44 which when covered with a membrane, forms sleeve 14.

The cross section of the wire used to fabricate the device can be in many shape, typically it will be round having a diameter of 0.05-1 mm. Fabrication of the device can be effected via braiding. Alternatively, other mechanical methods can be used for fabrication of the device, such as laser cut of a tubular member.

Figures 5A, 5B:
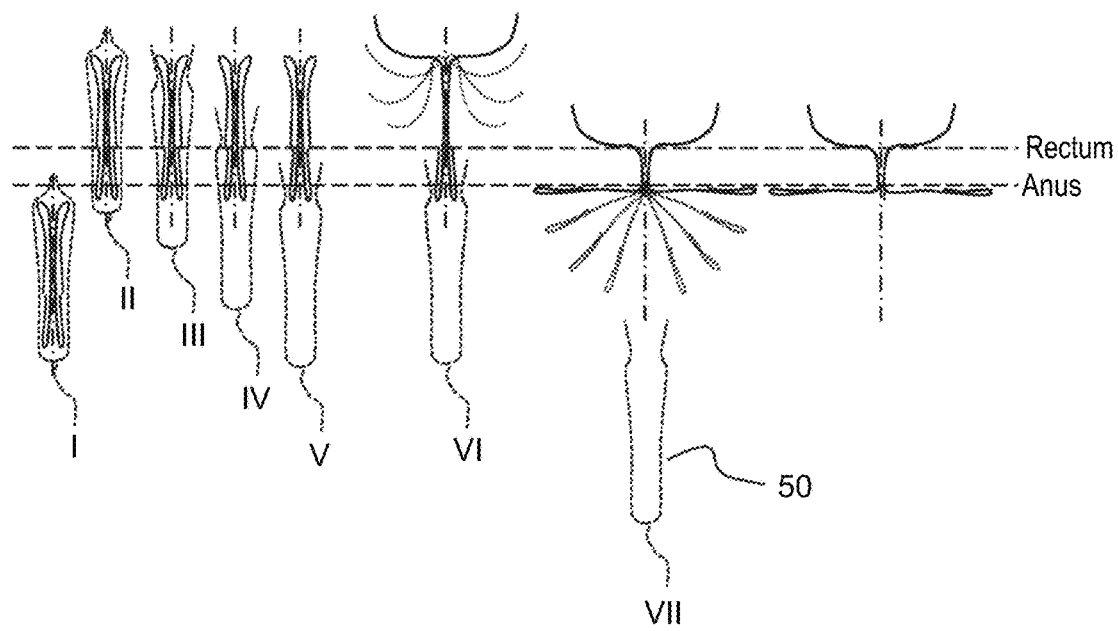
FIGS. 5A-B illustrate deployment of one embodiment of the present device (FIG. 5A, steps I-VII) with respect to a schematic illustration of the anal canal (FIG. 5B) showing (dashed lines) the anatomical landmarks targeted at which the device is positioned.

FIG. 5a illustrates deployment of device 10 using an applicator 50. For the purposes of clarity, deployment of device 10 (as shown in steps I-VI of FIG. 5a) is illustrated with respects to line boundaries defining the rectum and anus illustrated in FIG. 5b.

Device 10 is radially folded within an external applicator 50, having an external diameter of about 5-12 mm. Device 10 is advanced in its compressed state through the anus and into position (I-VI). Applicator 50 is then pulled out and device 10 expands in position. The anchoring of the device into its position, in its expanded mode, is achieved due to pressure applied to the upper skirt of the device 43. However, if the device is pulled out by pulling its proximal end 45, the distal/upper portion of the device collapses, thereby enabling easy extraction of the device following defecation.

FIGS. 6a-6d illustrate a device 10 that is activated via mechanical pulling of an inner structure 74. Device 10 includes an outer (mesh) structure 72 which is supported over an inner sleeve 74. When inner sleeve 74 is pulled out, outer structure 72 compresses and collapses downward as shown in FIGS. 6b-d, thereby deploying anchor regions 76 and 82 each having a typical cross section 78 and 80 respectively.

Outer structure 72 can be covered with an elastic sleeve (e.g. silicone or Teflon based material) for comfort.

When device 10 is in a pre-deployed mode, i.e. stretched and elongated over sleeve 74, it sized and configured (diameter of 5-12 mm) capable of insertion into the anal canal. Once positioned in the anal canal/rectum (FIG. 6*a*), inner sleeve 74 can be pulled out (FIGS. 6*b-c*) to collapse outer structure 72 and anchor device 10 in position (FIG. 6*d*). Outer structures 72, 76 and 82 can be fabricated from braided/laser cut elastic material such as Nitinol, stainless steel or polyester.

It will be appreciated that outer structure can be further strengthened by using longitudinal struts (not shown) similar to those described above with respect to FIGS. 2-3).

FIG. 7*a-*7*e* illustrate another embodiment of device 10 which employs a mechanical activation structure.

This embodiment of device 10 includes a mechanical fixture that converts a longitudinal pulling force (in the proximal direction) into radial expansion. FIG. 7*a* illustrates a cross section of device 10, while FIG. 7*b* illustrated a 3D model cut out.

The basic mechanical structure includes 2 sections: an internal activating unit 94 which is housed within an external folding unit 92. Unit 94 can include a stopper at end 98 which can be positioned against the external surface of the anal orifice.

When unit 92 is pulled out, it leads to folding of upper portion of unit 94 (as illustrated in FIGS. 7*c* and 7*d*). When unit 94 completely unfolds, unit 92 is fully folded as shown in FIG. 7*e*. Device 10 can include 4-12 mechanical structures which are radially distributed (evenly or not evenly) within sleeve 90. Sleeve 90 may include an additional spring-like coil (not shown) that provides a radial expansion force and ensure that the mechanical structures are radially pushed out and are biased against anal canal tissue.

As is mentioned hereinabove, the present device can be used to protect internal and optionally external hemorrhoids from the deleterious effects of physical straining and/or defecation and thus prevent swelling and/or prolapse and/or irritation of internal and optionally external hemorrhoids caused thereby.

The present device is inserted in its collapsed state into the anal canal (FIG. 8*a*). In its collapsed state, the device is typically 4-12 mm in diameter.

Devices which include a mechanical support (e.g. longitudinal struts), do not need an applicator. Such a device is inserted to the anal canal thru the anus, and advanced to position. The device can optionally include a ring at the proximal end that serves as a stop against the external surface of the anal orifice.

Devices, which do include struts or do not inherently have mechanical rigidity in the longitudinal axis, utilize an internal or external applicator. Such an applicator provides the device with the longitudinal rigidity necessary for pushing the device into position. An applicator can be a rod onto which the device is fitted, or a cover which wraps the device.

Once the device is positioned in the anal canal and rectum, distal and proximal anchors (e.g. balloon 26 and 20 of FIGS. 2*a-c*) are expanded (FIG. 8*b*), using for example, a pump which is connected to port 29 of device 10 shown in FIGS. 2*a-c*. The pump delivers a fluid (e.g. air, saline, water) to a final which does not cause discomfort to the user. When the user defecates, and the anal canal and rectum expand, the pressure applied by the device ensures that it is securely biased against the anal canal and rectum walls at a pressure level equal to the pressure delivered by the pump.

The pressure delivered by the pump is determined as follows:
Constant pressure level: where the pump has a single constant pressure level that is delivered to the device, and that level is maintained throughout the entire defecation process.
User adjustable pressure level: where the user can set the specific pressure level within preset limits.
Automatic pressure level: the pump analyzes the pressure delivered to the balloon anchors according to predetermined parameters, and adjusts the pressure accordingly. The pump can include a feedback and warning system that ensures that pressure does not exceed the compliance of the anal canal/rectum. Compliance of the GI tissue can be determined by dP/dV (where dP is the delta pressure built due to a change of dV in the volume of the fluid injected into the device).

Once defecation is completed, the pump is switched off or reversed and the fluid is drained from the device causing the device to collapse thus enabling removal and disposal by the user.

Device 10 of FIGS. 7*a-e* can be packed into an external applicator (not shown) having an external diameter of 5-16 mm. The packed system (device+applicator) is then positioned within the anal canal and rectum with stop 98 resting against. Unit 94 is then pulled out (FIGS. 7*c*, 7*d* and 7*e*) until unit 92 is deployed and sleeve 90 is biased against the anal canal. a lock 93 may be used to lock deployed unit(s) 92 in position. Upon defecation, device 10 conforms to the anatomy while providing a biasing force against the anal canal and thereby shielding the hemorrhoids. Following defecation, units 94 are pushed back in (distally) to unfold units 92 and enable removal of device 10 by the user.

FIGS. 8*a-b* illustrate anal delivery and deployment of one embodiment of the present device. The device, in its folded form, is inserted into the anal canal, such that the distal end of the device protrudes into the lower rectum (FIG. 8*a*). The device is then expanded (via any of the mechanisms described herein) to form the distal and proximal anchoring portions (dashed lines) which anchor the device within the anal canal and rectum.

Presently preferred configurations of the present device which is referred to herein as device 100 are shown in FIGS. 9*a-d*.

Device 100 includes a tubular body 102 (having a round or oval cross section) having flanged proximal and distal ends (104 and 106 respectively). Distal end 106 includes a balloon 108 which is constructed from a semi or non-compliant material such as nylon, silicon, Teflon or other applicable materials. Balloon 108 is an open or preferably closed toroidal balloon which encompasses most or preferably all of the circumference of tubular body 102. Balloon 108 can be glued/sutured to distal end 106 of tubular body 102 or alternatively, balloon 108 can include an integrated skirt 109 which is attached to tubular body via an adhesive, sutures and the like.

Tubular body 102 is preferably constructed from a polymeric mesh (e.g. polyester), using approaches well known in the art such as braiding, casting, or the like. The braided tube is then a heat treated to provide the tubular body with its final shape.

The mesh structure of tubular body 102 is preferably coated (e.g. laminated) with a soft polymeric material such as silicone or teflon in order to increase comfort. Such coating can also be used to lock or partially lock the junctions of the braid and hence increase the radial force of the braid while maintaining its flexibility. Alternatively, the junctions (all or portion) can be heat welded or glued. In addition, the internal surface of tubular body 102 can be coated with a low friction material such as Teflon embedded coating to facilitate passage of feces therethrough.

The coated mesh of tubular body 102 defines a lumen 110 (passageway) extending from an opening 112 at distal end 106 (defined by balloon 108) to an opening 114 at proximal end 104. Lumen 110 is sized and configured for passage of feces therethrough when device 100 is anchored within the anal canal and rectum.

The mesh and coating are configured such that tubular body 102 exhibits longitudinal integrity and radial compliance (preferably elastic). Radial compliance of tubular body 102 is preferably in the range of 10-40 mm of deflection per a pressure that is equivalent to 20-200 mmHg. Typical dimensions of device 100 are shown in FIG. 9b.

Device 100 is positionable and anchorable within the anal canal and bottom region of the rectum (region of transition from rectum to anal canal also referred to herein as the rectal neck). Anchoring of device 100 is effected via two mechanisms:

(i) rectal anchoring—when inflated (to 1-4 ATM) the diameter of balloon 108 is about 60 mm, 10 mm larger than a typical diameter of the rectum. As such, inflation of balloon 108 applies a radial outward force against the walls of the rectum thereby anchoring balloon 108 and sealing it against the rectal walls. In addition, due to the fact that balloon 108 is larger than the rectal opening to the anal canal (rectal neck), it also serves as a stopper against downward migration of device 100.

(ii) anal canal anchoring—the radial compliance and longitudinal integrity of tubular body ensures that when device 100 is positioned within the anatomy, tubular body 102 (which mostly resides in the anal canal) radially conforms to the anatomy and thus anchors thereto. At rest, the anal canal inner wall is characterized by folds of tissue and an irregular surface. The ability of tubular body 102 to conform to the inner surface of the anal canal provides an anchoring force. In addition, the polymeric coating of tubular body 102 can be selected to increase friction between an outer surface of device 100 and the tissue lining the anal canal and/or rectum.

Since device 100 is used for treating disorders of the anal canal and rectum, it is preferably configured to facilitate passage of feces through lumen 110 while remaining anchored in position. In order to provide stable anchoring at the rectal region during passage of feces through lumen 110, balloon 108 is shaped such that opening 112 is conical, i.e. it tapers in the proximal direction. Such a conical opening is preferably achieved by angling balloon 108 as shown in FIG. 9b.

Such tapering ensures that feces entering through opening 112 applies an outward radial force on balloon 108 further pushing it against the rectal walls thereby increasing the anchoring force which is determined by the pressure applied on the balloon and hence on the rectum walls, and the angle of the conical balloon. Such tapering also ensures that feces transitions into lumen 110 is smoother, and unobstructed.

Figure 9A:
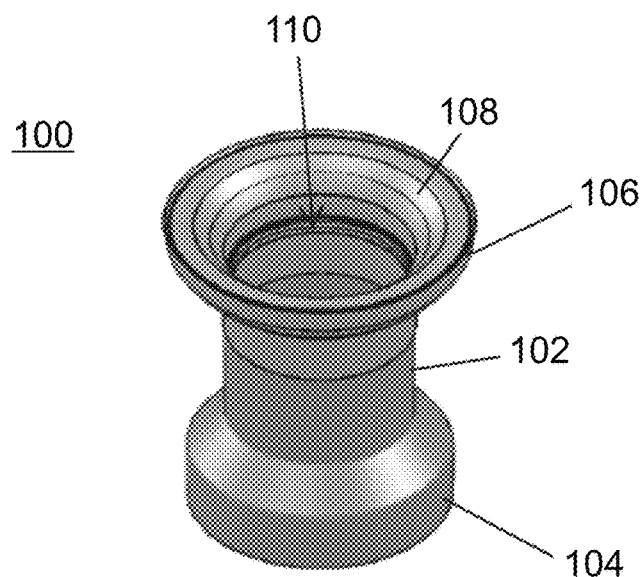
FIGS. 9A-B illustrate one preferred configuration of the present device, shown in an isometric view (FIG. 9A) and as a cross sectional schematic (FIG. 9B). In this configuration, the inflatable portion is conical.
Figure 9B:
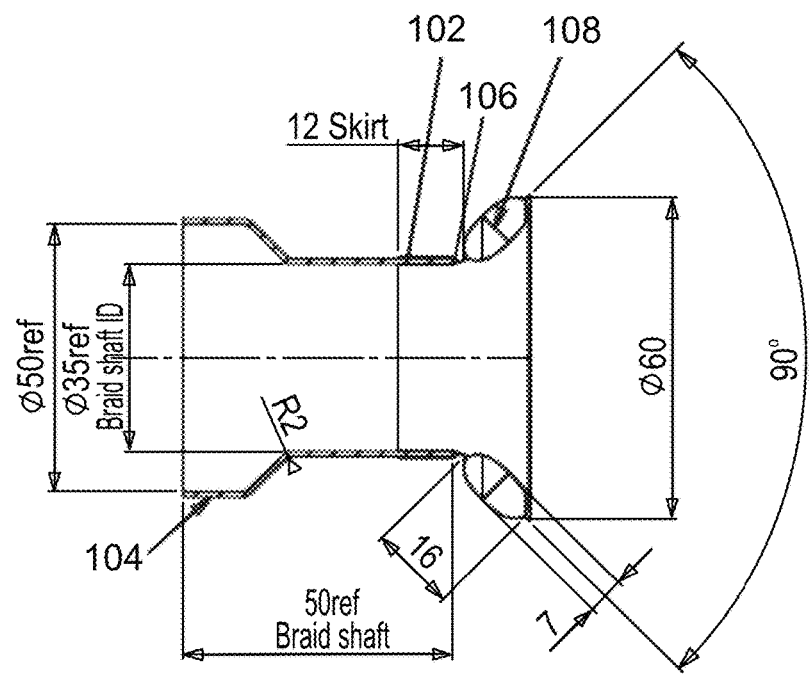
Figure 9C:
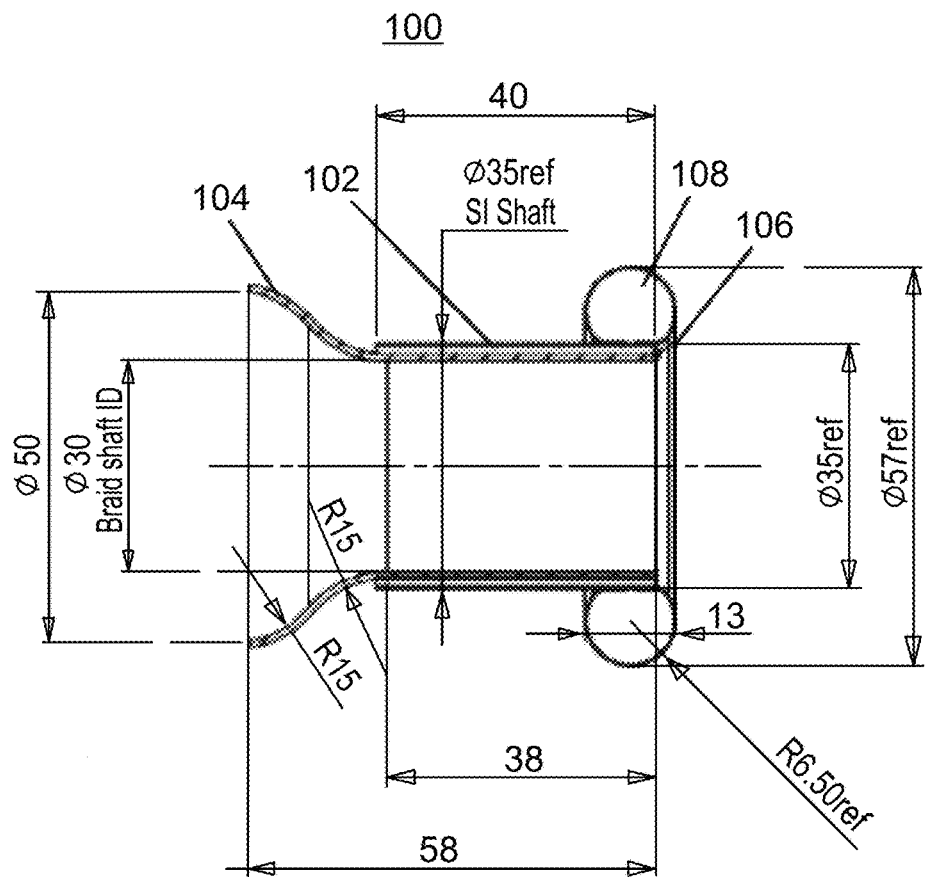
FIGS. 9C-D illustrate another preferred configuration of the present device, shown as a cross sectional schematic (FIG. 9C) and in isometric view (FIG. 9D). In this configuration, the inflatable portion is a compliant or a non-compliant balloon.
Figure 9D:
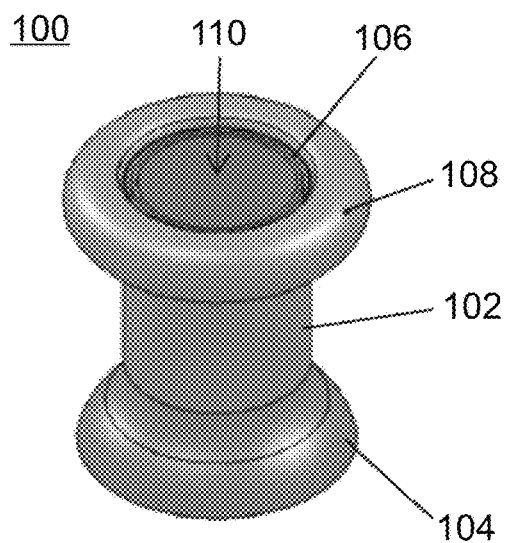

FIGS. 9c-d illustrate a device 100 which is similar in construction to device 100 shown in FIGS. 9a-b with the exception that balloon 108 is flatter and not conical in shape. In device 100 shown in FIGS. 9c-d, balloon 108 is toroidal in shape and conforms to the bottom of the rectal neck region, rather than the sides as is the case with device 100 of FIGS. 9a-b.

Device 100 can be delivered into the anal canal/rectum using a delivery device (applicator). Device 100 can be folded and compressed into the delivery device or it can be wrapped by a thin sheath which can be torn to deploy the device using a tear string, balloon inflation and the like. The applicator can be manually slid off the device prior to, or following inflation of the balloon anchor. Alternatively, the radial force generated by inflation of the balloon anchor of the device can rip the applicator and allow its release or push the applicator downward to facilitate release.

A prototype of device 100 (FIG. 14) constructed in accordance with the teachings of the present was tested in animal models. As is described in Example 3 of the Examples section which follows, this prototype firmly anchored in the animal rectum with the tubular body biased against anal canal walls. Defecation through the device was achieved without device movement, the animal did not show any signs of stress or discomfort.

The external surface of the present device can be coated with a powder, ointment or gel containing a drug such as a topical anesthetic (e.g., benzocaine), a topical steroid (e.g., hydrocortisone) or a topical vasoconstrictor (e.g., ephedrine sulfate) using approaches well known in the art.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Mesh/Balloon Prototypes

Prototypes based on a tubular mesh and/or balloon anchor were developed and tested for several parameters including flexibility (minimum and maximum folding/expanding diameter), biasing force, anchoring via pulling force out of an In-Vitro gig (that simulate the anal canal).

Figure 10:
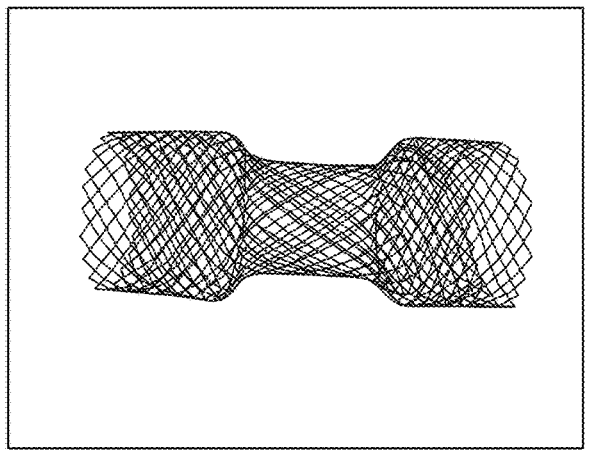
FIGS. 10, 11 and 12A-12B illustrate several prototypes of the present device used for testing device functions.

FIG. 10 illustrates a tubular mesh prototype constructed from a polyester material, formed by a braiding machine.

The tubular mesh was configured as an hourglass with the openings being 45-50 mm in diameter, the neck being 45 mm long and the opening in the middle of the neck being 25-30 mm in diameter. The mesh struts were configured to provide minimal compressibility and elongation in the longitudinal axis while maximizing compression and elasticity along the radial axis. To do so, the angle of the mesh was calculated, and few models each with other angle were produced. The effect of the angel was measured including the flexibility and biasing.

The prototype exhibited longitudinal stiffness and radial elasticity under a force equivalent to a radial pressure of 20-100 mmHg.

Figure 11:
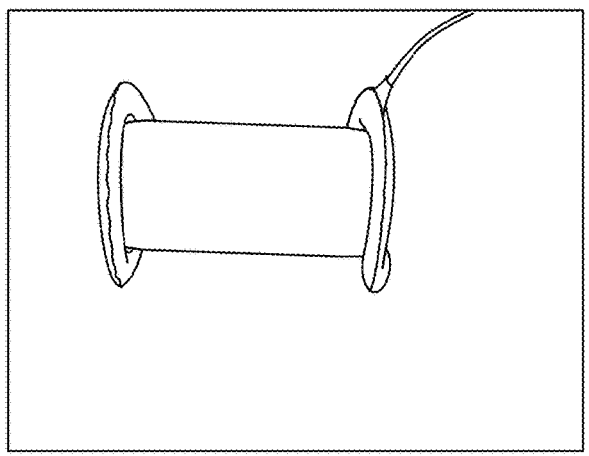

FIG. 11 illustrates a balloon-based device which includes two anchoring balloons flanking a tube. This prototype was fabricated from nylon with the following dimensions: overall length: 76 mm, diameter of tube: 35 mm, diameter of balloons 55 mm. A tube for inflating the balloons was attached to device.

Two types of balloons were tested, compliant (silicone) and non-compliant (polyurethane).

Example 2

Prototype with Balloon and Struts/Mesh

Figures 12A, 12B:
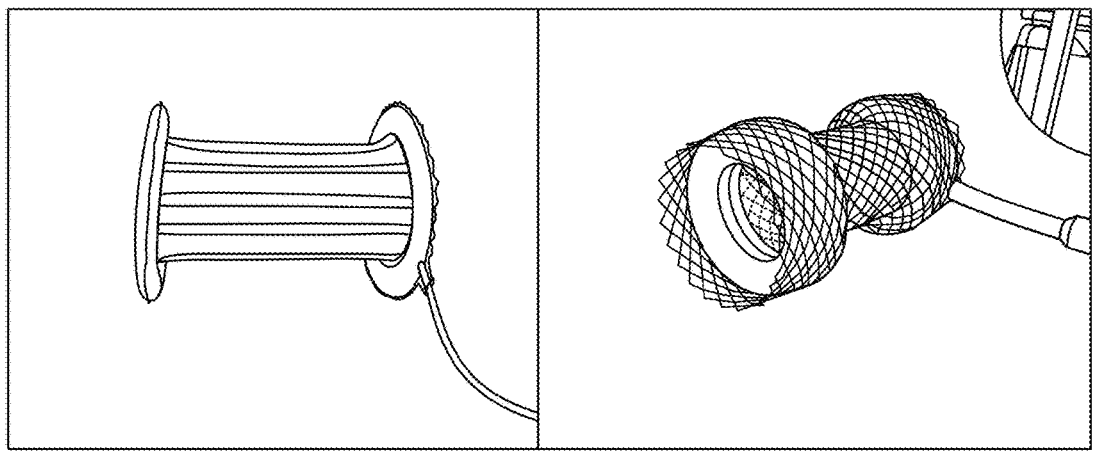

Prototypes combining struts (FIG. 12a) or mesh (FIG. 12b) for vertical support and radial compliance and a balloon anchor were designed and tested in vitro.

Each of the prototypes (strut-balloon or mesh-balloon) was loaded into the apparatus and anchored by inflating the balloon(s) to approximately 1 ATM. The apparatus was held steady and the prototype was pulled longitudinally via a force measurement system at a pulling force of approximately 1000 grams.

Next, each of the prototypes was tested for radial elasticity and the ability to conform to the anal canal anatomy.

A test apparatus (FIGS. 13a-b) simulating the anatomy of an anal canal was constructed and used to test anatomical conformation and anchoring.

The test apparatus included an inflatable balloon which enables radial closing and opening of the lumen of the apparatus.

Figures 13A, 13B:
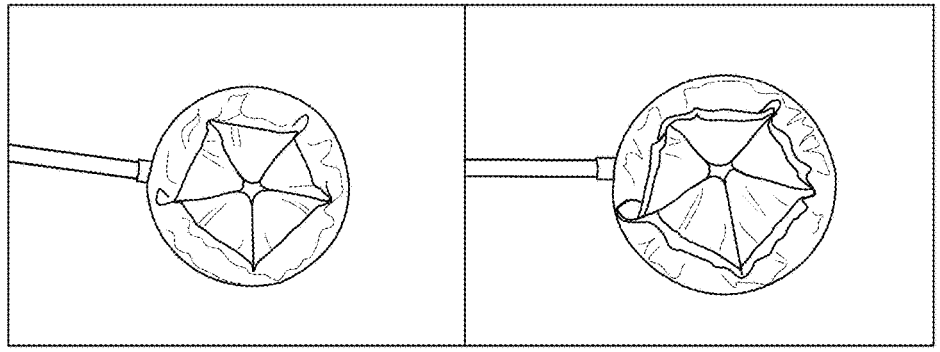
FIGS. 13A-B illustrate a testing apparatus simulating an anal canal in a closed (FIG. 13A) and closed (FIG. 13B) states.

The prototypes were inserted into the apparatus which was inflated to transition from a lumen opening diameter of 30 mm (FIG. 13b) to a completely closed lumen (FIG. 13a). Visual inspection of the prototypes in the testing apparatus enabled determination of device conformity and elasticity in the radial axis.

The prototypes were then subjected to a radial bias test simulating pressure of hemorrhoids on device. Pressure was applied to a sidewall of the prototypes and radial deformation was measured. This was effected in order to determine the radial pressure the prototypes can withstand without collapsing.

The benchmark pressure was set at 50 mmHg (~200 grams) which is slightly above the combination of the capillary (15 mmHg) and abdominal (30 mmHg) pressures. A deformation of no more than 5 mm (radially) was considered a good result.

Conclusions

Table 1 below summarizes device performance with respect to several functional parameters. The present study demonstrated that the present device prototypes provide excellent anchoring with an anchoring force of ~1 kg or more, and a radial biasing force of 200 grams (~50 mmHg) with only 5 mm of deformation. The stent-like braided tubular portion provided excellent radial elasticity without collapsing.

TABLE 1

|  | Stent/Braid | Compliant balloon | Non Compliant balloon |
| --- | --- | --- | --- |
| Deliverability | 3: requires thin struts, thin and elastic coating and good crimping | 2: non-compliant could be thin | 3: compliant could not be as thin as compliant but still can be very thin enough |
| Positioning | 2: size is "well-defined" | 3: Anchor balloon part needs to be well positioned | 3: Anchor balloon part needs to be well positioned |
| Expansion | 2: stent always want to expand | 3: distortion of balloon | 2: good/well shaped expansion |
| Anchoring | 2: coated struts provide excellent anchoring | 3: depends on rectum resistance | 2: "well-defined" size of anchor |
| Biasing/Shielding | 2: coated struts provide excellent biasing | 4: still Requires adding struts | 3: Balloon has strong structure, still Requires adding struts |
| Elasticity | 2: thin coating | 4: depends of struts design | 4: depends of struts design |
| Collapse/Release | 5 | 2: balloon is easily deflated | 2: balloon is easily deflated |

Example 3

In-Vivo Trials

Figure 14:
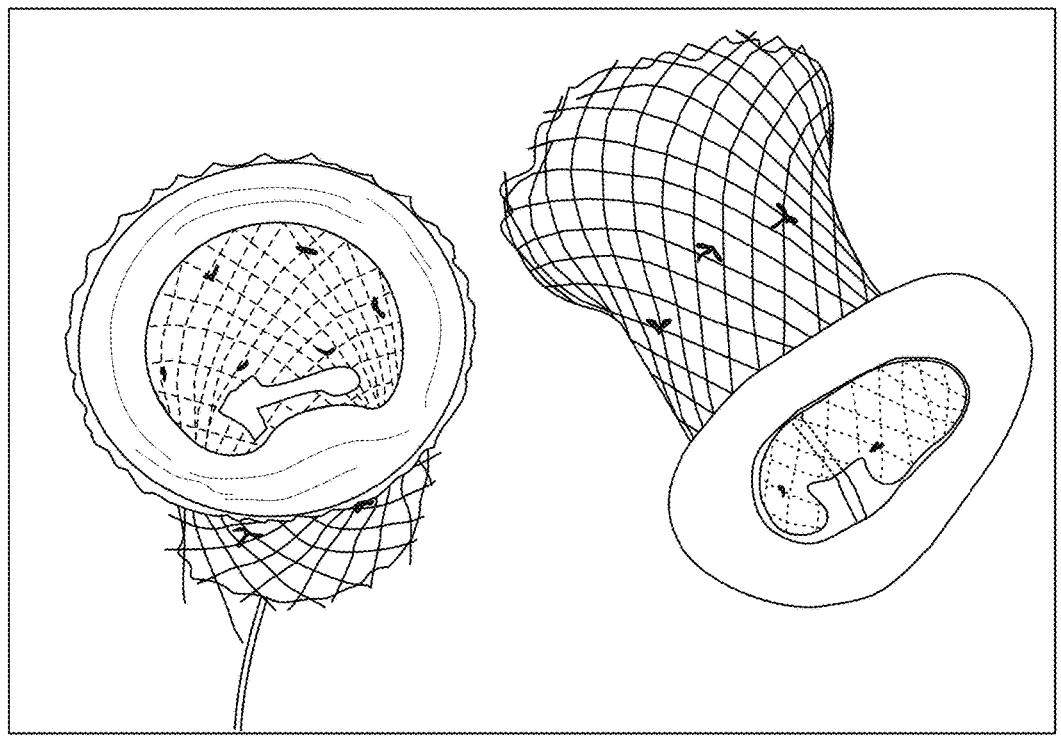
FIG. 14 illustrates an advanced stage prototype used for animal studies.

The prototype depicted in FIG. 14 was used for in-vivo tests. The device included an inflatable nylon balloon attached to a braided tubular body fabricated from polyester and coated with silicon. The balloon was inflated to about 2-3 ATM. Several balloon sizes (outer diameter) were tested—from 55 mm to 75 mm.

Figure 15:
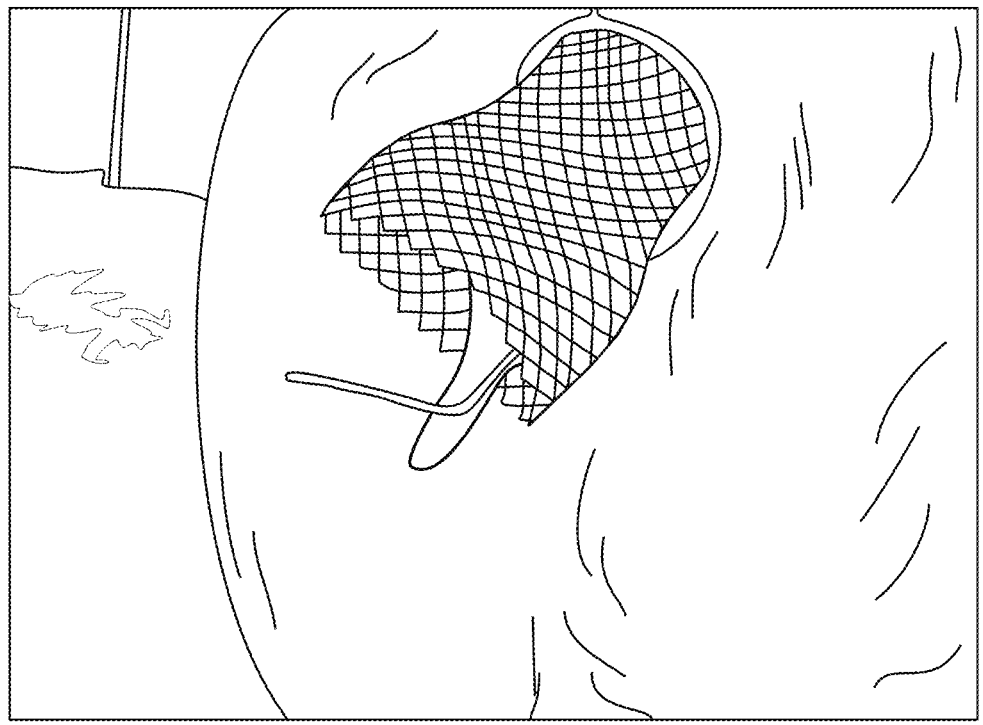
FIGS. 15-16 illustrate testing of the prototype of FIG. 14 in pigs.
Figure 16:
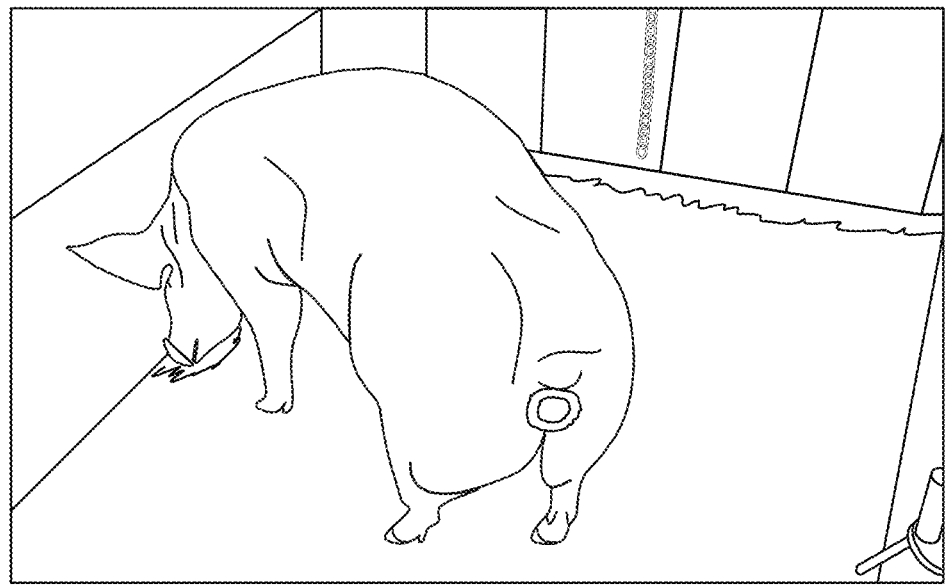

The tests were performed on a mature pig (weighting about 70 kg), with light anesthesia. The pig was very lightly sedated, the device was inserted and inflated and then the anesthesia was terminated and the porcine was released in its chamber (FIGS. 15-16).

Tests showed that the insertion of the device (lubricated) was very easy and simple, that the anchoring of the device was excellent—the device was not pulled out spontaneously and remained in place for hours (until removed). The elasticity of the device was very good, enabling normal defecation through the device on several occasions.

The pig showed no signs of stress or discomfort during any stage of the tests, and its behavior was entirely normal—through eating, defecating and even sleeping.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for reducing pain, bleeding and/or distension of hemorrhoids during defecation and optionally straining, comprising:

(a) a C-shaped discontinuous toroidal balloon configured for anchoring within a lower rectum of a subject when inflated, wherein ends of said balloon are attached via an elastic element capable of elastically stretching when fecal matter transmits through the discontinuous toroidal balloon; and (b) a tubular mesh structure being elastic along a radial axis thereof, said tubular mesh structure being attached to said balloon when inflated and being for extending through said anal canal;

wherein said balloon and attached tubular mesh structure define a passageway through the device when said balloon is anchored within said lower rectum, said balloon and said tubular mesh structure being radially expandable during defecation when fecal matter is conducted therethrough.

2. The device of claim 1, wherein said tubular mesh structure is shaped as an hourglass.

3. The device of claim 1, wherein said tubular mesh structure is coated with silicone.

4. The device of claim 1, wherein said tubular mesh structure is fabricated from polyester or nylon.

5. The device of claim 1, wherein said tubular mesh structure is fabricated from a metallic material selected from the group consisting of stainless steel, nitinol, and cobalt chromium.

6. The device of claim 1, wherein said balloon is a non-compliant balloon.

7. The device of claim 1, further comprising a tubular sheath for radially constraining said tubular mesh structure in a folded configuration.

8. The device of claim 7, wherein said tubular sheath includes a mechanism for releasing said tubular mesh structure from said folded configuration.

9. The device of claim 8, wherein said mechanism tears said sheath.

10. The device of claim 8, wherein said mechanism removes said sheath.

11. A system for treating constipation during defecation comprising the device of claim 1 and an applicator for positioning and deploying said device in an anal canal-rectum region of a subject.

12. The system of claim 11, wherein said applicator includes a lumen for containing the device of claim 1 in a folded configuration.

13. The system of claim 11, wherein said applicator includes a plunger for ejecting the device of claim 1 from said lumen.

14. The system of claim 11, wherein said applicator disengages from the device upon inflation of said balloon.

15. The device of claim 1, wherein said tubular mesh structure is glued, thermally bonded, welded or sutured to said balloon.

* * * * *